United States Patent [19]
Gustafsson et al.

[11] Patent Number: 6,038,913
[45] Date of Patent: Mar. 21, 2000

[54] DEVICE FOR DETERMINING THE LEVELS OF NO IN EXHALED AIR

[75] Inventors: Lars Erik Gustafsson, Hässelby; Gunnar Magnus Severus Persson, Lidingö; Stefan Per Axel Strömberg, Upplands Väsby, all of Sweden

[73] Assignee: Aerocrine AB, Sweden

[21] Appl. No.: 09/045,374

[22] Filed: Mar. 20, 1998

[30] Foreign Application Priority Data

Mar. 27, 1997 [SE] Sweden ................................. 9701150

[51] Int. Cl.⁷ .......................... G01N 33/497; A61B 5/08
[52] U.S. Cl. ............................................. 73/23.3; 600/531
[58] Field of Search ............................. 73/23.3, 23.21; 600/531, 532, 343

[56] References Cited

FOREIGN PATENT DOCUMENTS

WO 95/02181  1/1995  WIPO .

OTHER PUBLICATIONS

Publication entitled: "An introduction to human physiology", by J.H. Green, 3rd Edition, Oxford University Press, London, Chapter 5, pp. 63–74, "Respiration".

*Primary Examiner*—Daniel S. Larkin
*Assistant Examiner*—Jay L. Politzer
*Attorney, Agent, or Firm*—Banner & Witcoff, Ltd.

[57] ABSTRACT

A device for determining the level of nitric oxide in an exhaled airstream belonging to a living organism selected to have its lung function evaluated, where an initial device is arranged to determine the current portion of nitric oxide and/or the distribution of nitric oxide over time during an exhalation phase. During the commencing period of the exhalation phase, the exhaled air is arranged to pass with no or with only a very small resistance or back-pressure to a free space, and during the remaining period, the exhaled air is arranged to pass through the initial device against the action of a suitable resistance or back-pressure. The level of nitric oxide is measured during this remaining period.

19 Claims, 2 Drawing Sheets

DEVICE FOR DETERMINING THE LEVELS OF NO IN EXHALED AIR

TECHNICAL FIELD

The invention concerns a device for determining the levels of NO (The portion of nitric oxide) in a mixture of gases in exhaled air produced during the respiratory cycle of a living organism and thereby having the possibility to show and/or register that a current lung function of a lung or lungs or a part or parts thereof, belonging to a living organism selected to have its lung function evaluated is normal, or deviates from a pre-determined normal level.

The term lung function does not only mean the function of the lung itself but also encompasses the associated respiratory ducts.

THE PRIOR ART

As the present invention is based on an evaluation of nitric oxide (NO) formed in organisms with lung functions, it can be mentioned initially that it is previously known that endothelial cells on the inner surface of blood vessels produce nitric oxide in the body.

It is also previously known that nerve cells and inflammatory cells can produce nitric oxide.

The invention is based on the fact that alveolar cells, the respiratory tract epithelium or another type of cell in contact with the lung's or the respiratory tract's airways produce endogenous nitric oxide and that this nitric oxide is secreted into the air in the respiratory ducts and/or lungs. It is therefore obvious that this portion of secreted nitric oxide can be measured in exhaled air.

In addition, the invention is based on the knowledge that an evaluation of this production of endogenous nitric oxide in the lungs and respiratory ducts provides a measurement of the condition and/or function of the lungs and respiratory ducts, i.e. the lung's condition or function, and that additions to this nitric oxide production are unlikely to emanate from other organs in the body because the nitric oxide so produced would immediately bind to the blood's haemoglobin and then be subsequently broken down.

Furthermore, the invention is based on the knowledge that the portion of nitric oxide in exhaled air is affected by different factors, where the endogenous nitric oxide formed has a special significance, but where consideration must even be given to other factors such as bacterial toxins, the level of oxygen or portion of carbon dioxide in inhaled or exhaled air or gases, or an inflammatory condition caused by tissue damage, the influence of chemicals, or activation of the immune system.

Consideration must also be given to the nitric oxide that is provided or substances that are donors of nitric oxide.

In support of this inference, it can be mentioned that practical experiments clearly indicate that a measurable level of nitric oxide is present in exhaled air when clean air is inhaled and that the measurable production of nitric oxide in the lungs can be blocked by inhibitors of nitric oxide synthesis. An increased level of nitric oxide can be demonstrated when nitric oxide donor substances are provided, e.g. nitro-glycerine. Expanding the respiratory ducts and lungs by, for example, use of positive expiratory pressure, will also increase the amount of exhaled nitric oxide.

Experiments on animals have also shown that if the blood circulation is stopped and the lungs are ventilated with a respirator, an amount of nitric oxide measurable in the expired air is still produced. This suggests that the alveolar cells, the respiratory tract mucous membranes cr other cells in direct or close association with the lung's respiratory ducts have an active role in the formation of nitric oxide, and that this takes place independently of, or in addition to, the previously known formation of nitric oxide in endothelial cells and which is considered to be stimulated by the flow of blood.

It can also be assumed that nitric acid is even formed endogenously along the whole breathing pathway, i.e. in the oral cavity, in the sinuses, in the nose, in the trachea past the larynx, in the bronchia and within the "free space" in the lungs, as well as in the lung's inner blood-filled parts.

As the present invention is based on being able to determine relatively small quantities of nitric oxide, it is worth mentioning that it is, in fact, previously known that levels of nitric oxide in a gas have been evaluated with the help of chemi-luminescence, for example by using the Monitor Labs' 8840, $NO/NO_2$ analyser, marketed by Oleico AB, Lidingó, Sweden.

Nitric oxide can also be demonstrated by collecting it in distilled water containing an iron (II) sulphate additive, freeze-drying to a dry state and then demonstrating it as nitrite, either with the diazo-reaction according to Martin et al, or with the Niturtest qualitative nitrite stick.

Even previously known measurement instruments that employ mass spectrometry can be used for this task, as can electrochemical cells or techniques that employ ia-red light absorption with the use of White cells.

As the present invention is intended to evaluate current lung function, it should in fact be mentioned that testing the function of a lung or lungs belonging to a living organism such as a human or an animal selected for lung function testing is previously known, and that this can take place by intravenously introducing a tracer gas and thereafter determining the concentration and distribution over time of the tracer gas in the exhaled air of one or more exhalation phases.

As the present invention is intended to evaluate current lung function, it should in fact be mentioned that testing the function of a lung or lungs belonging to a living organism such as a human or an animal selected for lung function testing is previously known, and that this can take place by inhaling tracer gas and thereafter determining the concentration and distribution over time of the tracer gas in the exhaled air of one or more exhalation phases. Nitric oxide is one example of such a tracer gas.

As the present invention is intended to evaluate current lung function, it should in fact be mentioned that testing the function of a lung or lungs belonging to a living organism such as a human or an animal selected for lung function testing is previously known, and that this can take place by utilising a tracer gas produced in the body as a whole and thereafter determining the concentration and distribution over time of the tracer gas in the exhaled air of one or more exhalation phases. Carbon dioxide is one example of such a tracer gas.

When these previously known methods are used, the shape of the curve representing the distribution of the tracer gas in the exhaled air over time is the decisive element in evaluating the lung capacity or function; a steep curve indicates a better lung function than a flatter. more gradual curve.

Patent SE-A-468,416 (equivalent to U.S. Pat. No. 5,447, 165) shows and describes a method and a device for being able to confirm current lung function of a lung or lungs belonging to a living organism selected for lung function testing by measuring the portion of nitric oxide in exhaled air.

The present invention can be considered to represent a further development of what is known through the said patent.

The contents of patent PCT/SE94/00659 (WO 95/02181) that shows and describes system for measuring levels of nitric oxide in exhaled air are also relevant to the prior art. When the levels of nitric oxide are abnormally high, this can be interpreted as an inflammatory condition in the respiratory tract.

From the publication "An introduction to human physiology" by J. H. Green, 3rd edition, Oxford University Press, London, Chapter 5 "Respiration", it is also previously known. particularly from page 72 and FIG. 98, that an exhalation phase can take place against a back-pressure by allowing the whole exhalation phase to take place through a narrow tube.

FIG. 99 in the same publication is intended to illustrate the possibility to, during the exhalation, first fill an initial balloon with air from the "dead space" and a part of the alveolar air with a second balloon closed-off, and thereafter close-off the flow to the said initial balloon and collect the remaining exhaled air of the exhalation phase, which comprising the alveolar air, in a second balloon. In this case, the contents of oxygen and carbon dioxide are determined. In the filling of both these balloons, the patient breaths against a considerable resistance or back-pressure. Further, the balloon does not provide a distinct end-point determining the exhaled volume.

With regard to the measures associated with the present invention, it can be mentioned that from the publication "American Journal of Respiratory and Critical Care Medicine", Vol. 155, 1997 in the article "Marked Flow-dependence of Exhaled Nitric Oxide" by Philip E. Silkoff et al. page 260–267, breathing against a back-pressure during the whole exhalation phase by utilising a resistance to flow is known.

ACCOUNT OF THE PRESENT INVENTION TECHNICAL PROBLEMS

Among the aspects that a person with skills appropriate to this area must consider to solve one or more of the technical problems posed, is partly an initial insight into those measures and/or sequence of measures that need to be taken, and partly the choice of the means required. For this reason, the following technical problems are probably relevant when achieving the object of the present invention.

With regard to the technique's prior art such as described above, it must be considered to be a technical problem for a device intended to determine the level of nitric oxide during one or more exhalation phases to create the pre-requisite conditions so that the determination is focused only on one part of tie nitric oxide's variation over time during the whole exhalation phase, and then on that part where the nitric oxide portion can be considered to be constant or essentially constant.

It is thus a technical problem to perceive the pre-requisites needed to be able to utilise only that portion of nitric oxide that is present and measurable at the concluding phase of exhalation.

Likewise, it should also be considered an technical problem to perceive of the pre-requisites needed to create a curve shape for the nitric oxide's variation over time during one or more exhalation phases where the current portion of nitric oxide can be determined with good accuracy, i.e. a determination of the current nitric oxide level present within a "flat area" of the nitric oxide's distribution during the exhalation phase.

There is thus a technical problem in being able to create such pre-requisites in a device like that referred to initially so that a required or, alternatively not required, measurement of the portion of nitric oxide can take place with a small back-pressure during a short commencing phase of exhalation, and with a greater back-pressure during a suitable part of the remaining exhalation phase, during which time the relevant measurement of the portion of nitric oxide takes place.

It is also a technical problem to be able to design the measuring device so that it can be used with advantage by persons with breathing difficulties, such as those suffering from asthma, as persons with breathing difficulties like asthma have been shown to have significant problems in exhaling against a continuous back-pressure provided by, for example, a narrow tube or a calibrated breathing gauge.

There is also a technical problem in allowing a complete exhalation phase beginning with a deep inhalation to be divided in time into two component parts, the first where exhalation takes place with no back-pressure or against only a extremely limited back-pressure when no measurement of nitric oxide relevant to the determination takes place and where the air contained in the "dead space" is expired, and the second where exhalation occurs against a suitable back-pressure and when the measurement of nitric oxide relevant for the determination takes place.

Likewise, it is a technical problem with a device such as that referred to initially to adapt the exhalation flow and/or speed, in this case during the second part of exhalation, so that reliable measurements are obtained even for persons with breathing difficulties.

Additionally, it is a technical problem for a device that shows and/or registers if the current lung function of a lung or lungs belonging to a living organism selected for lung function testing is maximal, normal or if deviates from the maximal or normal values, to be able to appreciate its significance by only, or as in this case, by primarily measuring the appearance of volume and/or time changes in the distribution of the portion of nitric oxide in exhaled air during one or more exhalation phases, and in addition to be able to appreciate its significance by creating such pre-requisites during exhalation so that during the commencing phase of exhalation, the exhaled air is arranged to directly pass into free space, while during the concluding phase thereof be arranged only to pass through an initial device that is arranged to evaluate current and relevant portions of nitric oxide and/or its distribution over time.

There is a technical problem in being able to decide if the significance of, and the advantages associated with, allowing the said first commencing phase to represent a volume or time that is chosen to exceed the volume for the "dead space" such as the volume for the mouth, nose, throat and bronchus of the organism, by a suitable factor It must then be considered to be a further technical problem to be able to decide if every discrepancy that appears in a comparison between the maximal plateaux-like region related to the portions of nitric oxide, irrespective of whether this is a positive or a negative difference, should be interpreted as a change, commonly a deterioration, of the lung function.

Taking into consideration the fact known previously that it requires about 7–10 seconds for about 90% of inhaled nitric oxide to be taken up by the blood in the lung's most peripheral sections known as the alveoli, and that it has therefore been suggested that, with regard to among other things the surrounding air's possible content of nitric oxide, a reliable measurement of exhaled nitric oxide requires the provision of pure air from, for example, a gas supply by way of a three-way valve, it will probably be a technical problem to be able to utilise the fact that the uptake of nitric oxide is much more effective than has previously been assumed, with 99% uptake of the inhaled amount, so that levels up to 10 ppm are reduced to 100 ppb within 2–4 seconds.

There is even a technical problem in being able to take into consideration the fact that by efficiently taking up nitric oxide in the alveoli, essentially nitric oxide-free air is created within the space of a few seconds, so that this air can then be exhaled with only the provision of the body's own nitric oxide secreted from the lung's or the respiratory tract's cells, and that in this way, the nitric oxide can be measured reliably in the exhaled air.

When that happens, it is especially advantageous if the nitric oxide remaining from the inhalation phase can quickly be "washed out" by an initially more rapid phase of exhalation, after which the level of the body's own exhaled nitric oxide can be measured with greater reliability during the later and, due the provision of a back-pressure, slower phase of exhalation.

A further advantage is that no special supply of gas is then required.

As well as the need for a simple method to separate inhaled nitric oxide from that produced by the body and exhaled, there is also the problem of being able to differentiate between inhaled nitric oxide present in the lower respiratory duct that originates in the nose, mouth and throat and that is later exhaled, and nitric oxide generated in the lungs and associated lower tract that is also present in the exhaled air.

In addition, it is a technical problem to be able to observe with simple means that, like the nitric oxide supplied from the surrounding air, the nitric oxide from the nose, mouth and throat will be rapidly taken up by the alveoli and the remaining part "washed out" during the commencing phase cf exhalation, commonly by exhaling a volume equivalent to 1–10 times that of the "dead space" present in the respiratory ducts, preferably 4–8 times this volume.

A common way to estimate the size of an individual's "dead space" is to approximate it to 2 ml per kg of body weight, although certain deviations can occur with regard to physique, age, sex and the possible use of breathing aids such as tracheotomy or intubation tubing.

THE SOLUTION

To solve one or more of the technical problems named above, the present invention has as its starting point a device that is able to evaluate nitric oxide levels in an exhaled airflow and thereby be able to confirm current lung function, including respiratory duct function, or show current lung and/or respiratory duct functions in the lung or lungs or a part or parts thereof belonging to a livings organism selected for lung function testing.

To evaluate the portion of nitric oxide, an initial device is arranged so that it can determine the current portion of nitric oxide and/or the portion of nitric oxide distribution over time and/or volume during an exhalation phase.

The invention shows especially that, during the commencing period of the exhalation phase, the exhaled air is arranged to pass to a free space with no or with only a very small resistance or back-pressure, but that during the whole or part of the remaining duration, be arranged to pass through the said initial device against the action of a suitable resistance or back-pressure.

Furthermore, the invention suggests as proposed embodiments, that a volume of exhaled air from the commencing phase of exhalation is chosen so that it exceeds the volume of the "dead space", such as that in the mouth, nose and throat of the organism.

In addition, it is shown that the commencing phase of exhalation, following on from a deep inhalation phase, is chosen to be equivalent to a volume 1–10 times that of the "dead space', preferably 4–8 times and adapted to the size of the individual. It is also conceived, by the present inventors, that the volume can be chosen to a volume less than the estimated "dead space" of the patient, e.g. 0,2-1 times this volume The relevant measurement occurs during an exhalation phase that is ideally preceded by a deep inhalation phase, but only takes place during the second part of the exhalation phase, although with improved technology, it could even be carried out during a normal respiratory cycle.

A number of measurements and results taken during the whole or parts of the second part of several exhalation phases can be processed to give mean values.

By measuring the volume flow of exhaled air at the same time as measuring the level of nitric oxide, it is possible to determine the secretion of nitric oxide during the described plateaux-like region.

The back-pressure chosen after the commencing phase of exhalation is commonly 1–25 cm of water, preferably 3–15 cm.

The invention shows that a valve or equivalent can be controlled to switch between the initial and latter phases and is suitable for directing the exhaled air along one of two pathways.

The valve is arranged so that it can wholly or partly close-off a channel intended for exhaled air.

Such proposed embodiments within the scope of the invention show that the volume chosen for the initial phase can be contained, such as with the help of a gas-tight bag connected to an exhalation channel, and when the time has expired or a volume measured or similar and when the bag is filled, the exhalation phase takes place against a suitable back-pressure via the said initial device.

The invention also shows that if a discrepancy appearing between a normal or an individually modified stored value and a current measured value gives a negative value between the portions of nitric oxide related only to the plateaux-like region, it is possible to improve an impaired lung function or respiratory duct function and even fully restore an impaired lung function by supplying more or less oxygen to the inhaled air or otherwise adopting measures that allow a reduction in the portion of carbon dioxide in the body and/or the exhaled air.

It is also shown that if a positive value is noted when making a comparison of the portions of nitric oxide related to the plateaux-like region, an impaired lung function cannot be immediately restored but that this must be achieved by treatment. Examples of such treatment include overcoming bacterial or other kinds of infectious influences, activating the immune system, taking measures to remove irritating substances, overcoming inflammatory reactions, eliminating or reducing possible chemical reactions and/or providing pharmaceutical preparations or adjusting the supply of pharmaceutical preparations currently being administered.

However, if a discrepancy occurs towards the lower value for the plateaux region related to the distribution of nitric oxide levels over time, an impaired lung function can initially be compensated by overcoming bacterial or other kinds of infectious influences, activating the immune system, taking measures to remove irritating substances, using chemical means to slow the injurious effects of immunoreactions, and/or providing pharmaceutical preparations or adjusting the supply of pharmaceutical preparations currently being administered, eliminating or reducing the influence of the effects of restricted lung capacity or airflow, or eliminating or reducing the effects of G-forces or immersion, or dimensioning the effect of blood flow through the lungs.

ADVANTAGES

The advantages that can principally be considered to characterise a device in accordance with the present invention are that it has created the prerequisites to improve the evaluation of the plateaux-like region of nitric oxide levels for the distribution of nitric oxide over time, and is thus able to confirm current respiratory duct and/or lung function. As an alternative to the concentration of nitric oxide, the amount of nitric oxide secreted within the plateaux-like region can similarly be confirmed in a simplified manner.

For people with respiratory difficulties, the device offers an open commencing phase of exhalation with no or with only a very little resistance plus a concluding phase with a resistance or back-pressure that is adapted to suit the well-being of the person.

That considered principally to characterise a device in accordance with the present invention is stated ir the characteristics section of the following claim 1.

BRIEF DESCRIPTION OF THE FIGURES

A currently proposed embodiment displaying the significant features of the present invention is now described in more detail with reference to the enclosed drawings, where.

DESCRIPTION OF THE PROPOSED EMBODIMENT

Figure 1:
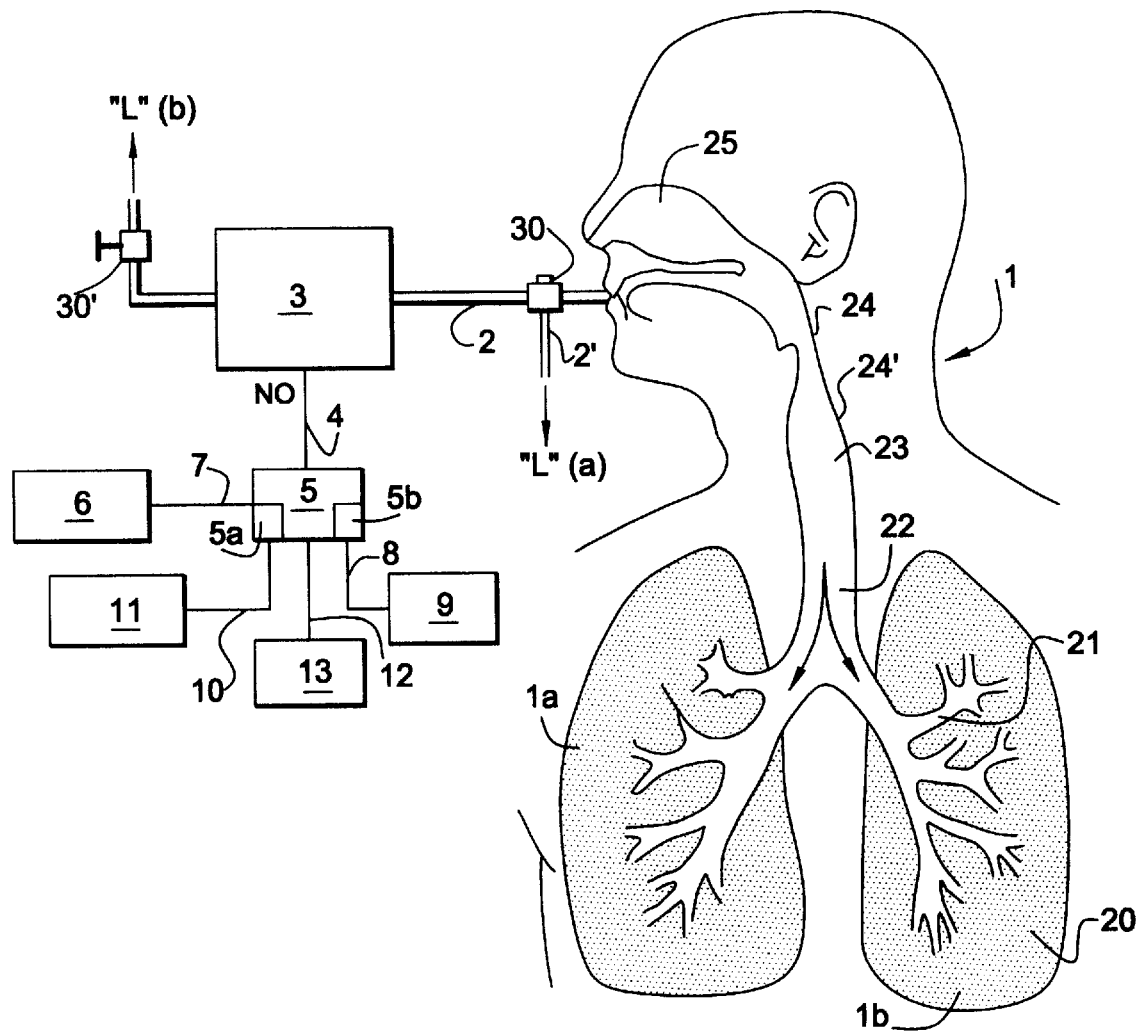
FIG. 1 shows a schematic illustration of a device according to the invention coupled to the exhaled air of a person whose lung and respiratory duct function are to be confirmed, and with the first embodiment of the valve device used.

With reference to FIG. 1, a schematic section of the respiratory tract of a person 1, with lungs 1a and 1b is shown.

The respiratory organ comprises the lungs with their respiratory ducts (alveoli, alveolar passages, bronchioles, bronchi) 20, larger intrapulmonary respiratory ducts (bronchi, bronchi segments and lobes) 21, the bronchial stem 22 and trachea 23, larynx 24 and throat 24', nose with sinuses 25, oral cavity 26.

Nitric oxide is produced in the mucous membrane and its associated secretions or adjacent parts in the whole of respiratory tract's respiratory ducts.

Particularly high levels can be attained if the air in the bronchi or in the nose and sinuses is allowed to remain stationary for a few moments.

In addition, nitric oxide can be introduced from the oesophagus joining to the throat behind the larynx by swallowing or belching.

The proposed embodiment concerns preferably measuring the level of nitric oxide (NO-level) or NO-amount in the lungs and their associated lower respiratory ducts within and around the lungs, i.e. areas 20 to 23 inclusive and minimising the influence of nitric oxide from the gastrointestinal tract and throat (24') as well as the nose and sinuses (25).

In addition, the influence on the measurement of nitric oxide inhaled from open air or nitric oxide generated in the oral cavity, nasal cavity, throat etc., and that remains in the "dead space" after completion of inhalation and that is initially expired during the commencement of exhalation is also minimised.

The "dead space" is the volume of inhaled gas that does not participate in the exchange of gases with the blood and is often the same as the volume of spaces 20 to 25 or 26 depending on whether breathing takes place via the nose or mouth, but which in healthy individuals excludes that part of volume 20 that is occupied by the alveoli as this is actually the place where the gaseous exchange with the blood occurs.

The proposed embodiment concerns emptying the "dead space" of inhaled and possibly contaminated gas to allow measurement of nitric oxide formed in the lungs and respiratory ducts during the exhalation phase, when essentially NO-free gas is expired from the alveoli and passes the "dead space" with its continuous production of NO.

Figure 2:
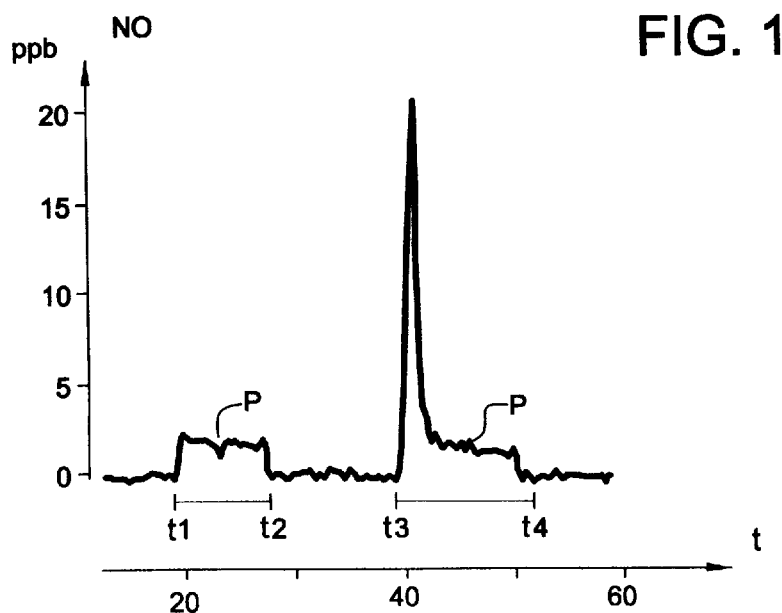
FIG. 2 shows as a graph, two examples of the portions of nitric oxide and their distribution in exhaled air over time during a exhalation phase.

FIG. 2 shows an example of NO concentration determined over time during two exhalation phases of a living organism.

The exhalation time is found between time points t1 and t2 and t3 and t4 respectively and can be assumed to be 8 seconds and 12 seconds and preceded by a deep inhalation phase.

The exhalation during time interval t1 to t2 has taken place following inhalation only through the mouth, while the exhalation during time interval t3 to t4 has taken place following inhalation through both the mouth and the nose.

For the course of both exhalations, FIG. 2 an illustrates a commencing phase with moderately increased or an extremely increased values for the portion of nitric oxide (NO-portion).

This commencing phase as illustrated applies to that volume of air that has been stationary in the respiratory duct and that has taken up large amounts of nitric oxide from, among other things, the mouth and nasal cavities.

The concluding phase is a more plateaux-like region "P" and represents the share of nitric oxide that is taken up by the air stream flowing through the respiratory duct.

The invention is based on being able to utilise and measure in a relevant way, the portion of nitric oxide that appears only within the plateaux-like region "P".

The device shown according to the invention features a tube 2 for exhaled air and that is connected at one end to an initial device, a measuring instrument 3, suitably of a nature described in more detail in the introduction, and that is connected at the other end to the mouth or nose, i.e. to the open end of the respiratory duct.

It is suggested that special measuring equipment that utilises mass spectrometry, electrochemical cells, chemiluminescence or light adsorption be used as measuring instrument 3.

As such equipment is previously known, no detailed description of such equipment's design or function will be given.

It is suggested, however, that a cable 4 carries a signal that signifies the portion of nitric oxide measured in the exhaled air, such as directly proportional to this value, and that this signal can be used directly for showing on a display of the measuring equipment.

The embodiment according to FIG. 1 does, however, show that this analogue or digital signal can be subjected to signal processing.

Here, the signal is shown connected to a comparator 5.

A device 6 or a memory is adapted to store the information required for a comparison in the comparator.

It can thus be advantageous if the memory 6 contains data for a plateaux-like region that is equivalent to different types of standard values or data related to the persons.

In particular, it is suggested that the memory 6 should contain stored values equivalent to the normal (preferably standardised) lung function or values related to persons providing measured values during one or several (immediately) preceding evaluations.

In this way, it is suggested that with the help of the device 6 and the cable 7 connected to it, information can be entered into the comparator 5 that can be used to advantage to represent the current person 1 and the standardised and maximum portions of nitric oxide for complete lung function.

Within the scope of the invention, it is also possible to store in device 6 a distribution of nitric oxide over time, especially in the plateaux-like region.

If this comparison between stored plateaux-like value or a related approximated value and the value measured at that moment gives a negative value, a signal is sent along cable 8 to a device 9 via a device 5b.

Should the value of such a comparison be positive, a signal is sent along cable 10 to a device 11 via a device 5a.

Should the value of such a comparison be zero or close to zero, a signal is sent along cable 12 to a device 13 to thereby show a complete or unchanged lung function.

Each discrepancy that appears during the said comparisons in comparator 5 can be interpreted as a change, usually a deterioration of the lung function.

For a more detailed understanding of such a device, refer to the patents named in the introduction, where even the function of the respiratory ducts is covered.

Figure 3:
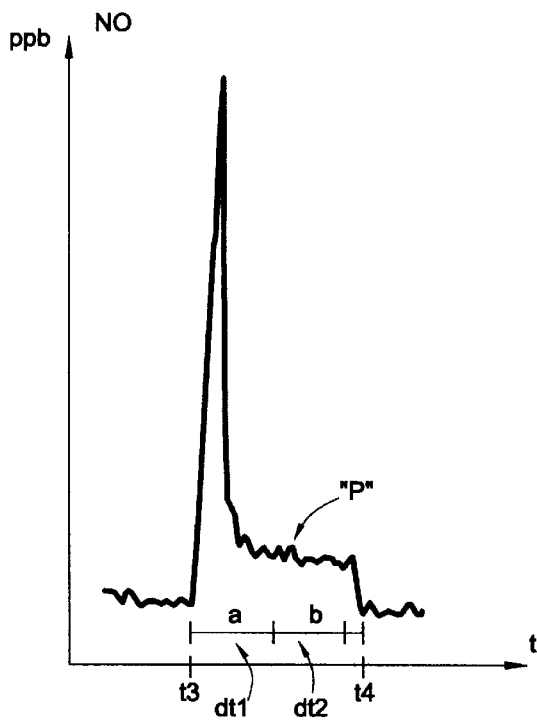
FIG. 3 shows the variation in nitric oxide levels over time with a time distribution according to the invention.

FIG. 3 shows in greater detail the distribution of nitric oxide over time between time positions t3 and t4 (luring an exhalation phase.

During the commencement "a" of the exhalation phase t3–t4, the exhaled air is arranged to pass with no or only very little resistance or back-pressure to a free space (the outside air) to release the volume of air in the respiratory ducts, while during the rest of the duration "b" the exhaled air is arranged to wholly or partly pass through the said initial device 3 against a suitable resistance or back-pressure.

Even if the switching between the first time interval "dt1" and the second time interval "dt2" can be controlled by the shape of the nitric oxide curve within the interval "dt1", it is suggested that control takes place with the help of a flow meter that switches over after a pre-determined volume, such as 0.5–1.0 liter. Control can also take place with the assistance of a specially selected time.

Satisfactory values can be acquired from measurement times of 1–3 seconds and therefore only a part of the plateaux-like region need be utilised. Persons with severe breathing difficulties can expect shorter measuring times during increased back-pressure.

The invention shows as one embodiment in FIG. 1, the use of a tube 2 fitted with a 3-way valve device 30 or equivalent positioned between the mouth 26 and the measuring instrument 3.

The valve device assumed here allows exhaled air "L" to pass out freely (L(a)) in its initial position and curing time interval "a" via the tube 2, while in its second position and during time interval "b", allows the air (L(b)) to preferably pass through the measuring instrument 3. (On that occasion, tube 2' is closed-off or practically closed-off).

FIG. 1 also shows the presence of a choke valve 30' for outgoing exhaled air L(b) that is active during the second time interval "b" to thereby regulate the back-pressure to a suitable value.

Several other different embodiments can be envisaged, some of which are described with reference to FIGS. 4 to 6.

The initial time interval "a" of the exhalation phase is chosen to be equivalent to a volume that is 1–10 times that of the "dead space", preferably 4–8 times.

Relevant measurements in instrument 3 occur during the exhalation phase and only during the second interval "b", where the value related to the plateaux-like region is quite constant and easy to evaluate.

Several measurements taken during the second interval "b" can be processed to give a mean value.

The back-pressure during interval "b" can be selected as 1–25 cm water, preferably 3–15 cm and, to attain comparable values, exhalation should take place against the same back-pressure.

The valve device 30 according to FIG. 1 can be arranged as one initial alternative to lead the exhaled air "L" to open space during an interval when the valve device was provided with a controlling signal or a pre-determined delay according to a controlling pulse from a control unit (not shown).

Figure 4:
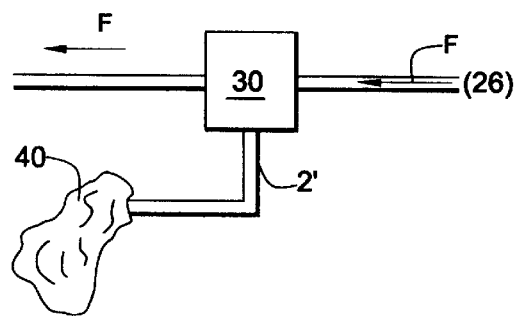
FIG. 4 shows a second embodiment of the valve device.

The embodiment in FIG. 4 shows that tube 2' is connected to an empty, gas-tight bag 40 that initially "a" is to be filled with a certain volume of exhaled air.

FIG. 4 is intended to show that during the commencement phase of the initial part "a" of exhalation, the exhaled air is arranged to pass to a free volume within bag 40, while during the rest of the time interval "b", the exhaled air F is arranged to pass to the said initial device 3.

The said free volume in bag 40 is chosen so that it exceeds the volume of the mouth, throat and respiratory ducts (the "dead space") of the organism by a selected factor.

When bag 40 is filled, the remainder of the exhalation phase can only take place against a suitable back-pressure, such as that regulated by the choke valve 30'. The gas-tight bag 40 is chosen so that when filled, it is quite unyielding and thereby able to give a fast transfer to the second period "b".

Figure 5:
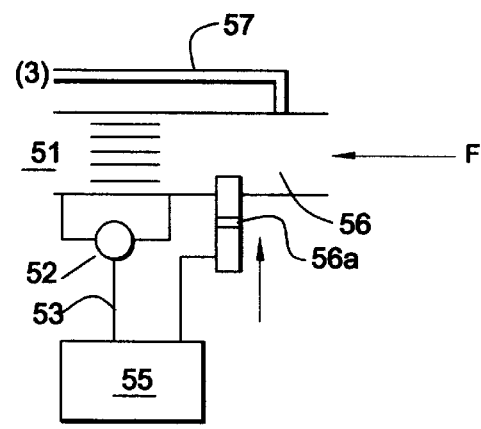
FIG. 5 shows a third embodiment of the valve device and FIG. 6 shows a fourth embodiment of the valve device.

FIG. 5 shows an alternative valve arrangement 50, where one exhalation tube 51 is provided with a flow meter 52 that is connected with a control unit 55 via a cable 53, and where this control unit 55 is adapted to activate a sliding valve 56 at a pre-determined volume "a', so that this valve shifts to completely (or in certain cases partially) close and shut-off exhalation tube 51 so that the subsequent exhalation air during period "b" passed through a narrow tube 57 to measuring instrument 3.

By a partial closure of sliding valve 56 due to a hole 56a arranged in the valve, a suitable division of exhaled air between measuring instrument 3 and the free space 51 can be achieved.

In an alternative embodiment, the sleeve and/or the tube 57 can be placed downstream from the flow meter 52.

Figure 6:
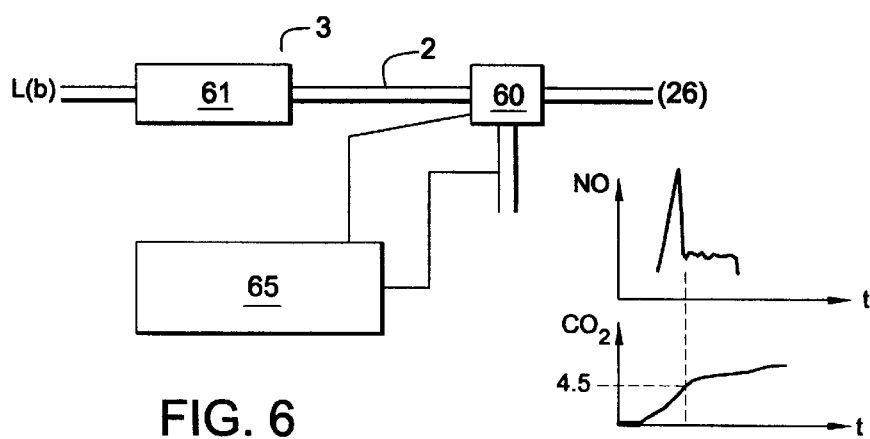

FIG. 6 shows an alternative valve arrangement 60 with what is known as a manually or automatically controlled valve device, where the tube 2 is provided with a suitable back-pressure by being coupled to a tube containing chemicals or an ampoule 61(3) adapted to give the required resistance and containing a chemical substance or material for the collection and/or preservation and/or demonstration of nitric oxide.

In addition, it can be mentioned that the nitric oxide values related to the plateaux-like region are dependent on the flow and on the control unit 55 in FIG. 5 being supplied with a correction factor in this respect. Increased flow gives a lower level of nitric oxide and vice versa, while the amount of exhaled nitric oxide diminishes somewhat with reduced flow.

The pressure in the breathing pathway does not, however, appear to affect the formation or secretion of nitric oxide.

"Dead space" can be assumed to be approximately 2 ml/kg body weight and the volume during time interval "a" should normally be selected to be under 20 times this volume, such as 1–10 times, or preferably 4–8 times. The internal volume of the apparatus/device up to the point of measurement should be added to this volume.

The flow rate through the measuring instrument 3 and especially during time interval "b" should be chosen so that a clearly easy-to-measure plateaux-like region is obtained.

The switching of valve device 60 between time interval "a" and "b" can also be controlled by control unit 65 by detection of the nitric oxide level in the exhaled airstream.

Here, switching can occur at values between 3–8%, preferably around 4.5%, as concentration increases with time according to the graphs in FIG. 6.

A comparable way of controlling valve device 60 can be to detect the portion of nitrogen or oxygen in the exhaled air, or the temperature or content of water vapour, or another substance that indicates that exhalation of the "dead space" volume typical for the individual has taken place. This control can also occur by measuring the nitric oxide that has been supplied to or gathered in the "dead space" during the rapid initial exhalation.

The invention is naturally not restricted to examples of embodiments such as those declared above, but can be modified within the scope of the invention illustrated in the following claims.

It is obvious for a person with an understanding of the area, that the effect of the immune reactions, infectious influences, chemical influences and tissue damage named in the claims, as well as the asthma, bronchitis and emphysema named in the preceding background information, and that can form part but not necessarily all of the individual's condition, cause inflammation in the lungs and/or respiratory ducts.

We claim:

1. Device for determining the level of nitric oxide generated within the body of a living organism in an exhaled airstream belonging to the living organism selected to have its lung function evaluated, said device including a measuring device arranged to determine a current portion of said generated nitric oxide and/or a distribution of said generated nitric oxide over time during an exhalation phase, a first fluid path which allows a first portion of exhaled air from the organism during a commencing period of the exhalation phase to pass with no or with only a very small resistance or back-pressure to a free space, and a second fluid path which allows a second portion of the exhaled air from the organism during a remaining duration of the exhalation phase to pass through said measuring device against a resistance or back-pressure so that the level of said generated nitric oxide in the second portion of the exhaled air can be measured.

2. Device according to claim 1 characterised by a volume of exhaled air during the commencing period of exhalation being chosen to exceed the volume of the dead space of the organism.

3. Device according to claim 1 characterised by a volume of exhaled air during the commencing period of exhalation being chosen to be less than 20 times that of the dead space.

4. Device according to claim 3 characterized by a volume of exhaled air during the commencing phase of exhalation being chosen to be 1 to 10 times that of the dead space.

5. Device according to claim 3 characterized by a volume of exhaled air during the commencing phase of exhalation being chosen to be 4 to 8 times that of the dead space.

6. Device according to claims 1, 2 or 3 characterised by said measuring device including measuring means for measuring the level of nitric oxide only during said remaining duration of the exhalation phase of a deep or normal breathing cycle.

7. Device according to claim 5 characterized by the back-pressure being chosen to be in the range of 3 to 15 cm of water.

8. Device according to claim 6 characterised by a number of measurements during the remaining duration of several exhalation phases being processed to give mean values.

9. Device according to claim 1 characterised by the back-pressure being chosen to be in the range of 1 to 25 of water.

10. Device according to claim 1 further including a valve that can be controlled to switch between a first phase and a second phase and that is adapted for directing exhaled air along one of the two paths.

11. Device according to claim 10 characterised by the valve being arranged to partly close-off a channel intended for exhaled air.

12. Device according to claim 11 characterised by the volume of the first phase being limited by an air-tight container connected to the exhalation channel.

13. Device according to claim 12 characterised by the container being capable of collecting gas and having its final volume adapted to be 1–10 times the volume expected of a dead space of a person.

14. Device according to claim 13 characterised by the remaining duration of the exhalation phase taking place against a suitable back-pressure once the container is filled.

15. Device according to claim 1 characterised by a shift between the commencing period and the remaining duration of the exhalation phase being controlled by a level of carbon dioxide in the exhaled air.

16. Device according to claim 1 characterised by shift between the commencing period and the remaining duration of the exhalation phase being controlled by a flow meter.

17. Device according to claim 9 characterised by a suitable back-pressure being selected only during the remaining duration of the exhalation phase.

18. Device according to claim 1 characterised by that the back-pressure during at least a portion of the remaining duration of the exhalation phase is selected to be identical on every occasion when comparable values are to be measured.

19. Device according to claim 13 further including a fluid restricting channel extending from an end of said gas collecting container and characterised by that the remaining duration of the exhalation phase occurs by the exhaled air passing through a suitable hole in said fluid restricting channel from the gas collecting container while the nitric oxide measurement takes place in an inlet to the gas collecting container.

* * * * *